United States Patent [19]

Charms

[11] Patent Number: 4,834,100
[45] Date of Patent: May 30, 1989

[54] APPARATUS AND METHOD OF DEFIBRILLATION

[76] Inventor: Bernard L. Charms, 2921 South Park Blvd., Shaker Heights, Ohio 44120

[21] Appl. No.: 862,034
[22] Filed: May 12, 1986
[51] Int. Cl.⁴ .............................................. A61N 1/36
[52] U.S. Cl. ................................ 128/419 D; 128/786
[58] Field of Search .................... 124/419 D, 784, 786

[56] References Cited

U.S. PATENT DOCUMENTS

| | | | |
|---|---|---|---|
| 3,144,019 | 8/1964 | Haber | 128/419 D |
| 3,236,239 | 2/1966 | Berkovits | 128/419 D |
| 3,566,876 | 3/1971 | Stoft et al. | 128/419 D |
| 3,605,754 | 9/1971 | Jaros et al. | 128/419 D |
| 3,614,955 | 10/1971 | Mirowski et al. | 128/419 D |
| 3,664,347 | 5/1972 | Harmjanz et al. | 128/419 D |
| 3,680,544 | 8/1972 | Shinnick et al. | 128/419 D |
| 3,738,370 | 6/1973 | Charms | 128/419 D |
| 3,857,398 | 12/1974 | Robin | 128/419 D |
| 3,942,536 | 3/1976 | Mirowski et al. | 128/419 D |
| 4,090,519 | 5/1978 | Pantridge et al. | 128/419 D |
| 4,168,711 | 9/1979 | Cannon III et al. | 128/419 D |
| 4,184,493 | 1/1980 | Langer et al. | 128/419 D |
| 4,270,549 | 6/1981 | Heilman | 128/419 D |
| 4,393,877 | 7/1983 | Imran et al. | 128/419 D |
| 4,559,546 | 12/1985 | Yip | 128/419 D |
| 4,559,946 | 12/1985 | Mower | 128/419 D |

OTHER PUBLICATIONS

Carr, J., "Defibrillators and Cardioverters"–Ch. 8, Servicing Medical and Bioelectronic Equipment, George Washington University, Feb. 1977.
CARDIO/PAK Series 936, Mennen–Greatbatch Electronics, Inc., Clarence, N.Y., pp. 1–4, 1–5 and 3–37 from Operation and Service Manual.
Lowan et al., The American Journal of Cardiology, Aug., 1962, pp. 223–233, "Comparison of Alternating Current with Direct Current Electroshock Across the Closed Chest".
Lown et al., JAMA, Nov. 3, 1962, "New Method for Terminating Cardiac Arrhythmias", pp. 150–157.
Balagot et al., J. Thoracic and Cardiovas. Surg., vol. 47, No. 4, Apr., 1964, pp. 487–504, "A Monopulse DC Current Defibrillator for Ventricular Defibrillation".
Shuder et al., Circulation Research, vol. XV, Sep., 1964, "Transthoracic Ventricular Defibrillation with Square-Wave Stimuli; One–Half Cycle, One Cycle, and Multicycle Waveforms".
DeSilva et al., Circulation, vol. 57, No. 4, Apr., 1978, pp. 827–830, "Energy Requirement for Defibrillation of a Markedly Overweight Patient".
Shuder et al., Circulation Research, vol. XiX, Oct., 1966, pp. 689–694, "Transthoracic Ventricular Defibrillation with Triangular and Trapezoidal Waveforms".
Harken et al., Medical Instrumentation, vol. 12, No. 1, Jan.–Feb., 1978, pp. 10–11, "Addressing the Issue of Dose Levels for Defibrillation".
Gold et al., Medical Instrumentation, vol. 12, No. 1, Jan.–Feb., 1978, pp. 20–23, "Comparison of Transthoracic Square–Wave Defibrillation Experience in the Dog and Calf".
Marchlinski et al., Annals of Internal Medicine, vol. 104, No. 4, pp. 481–488, Apr., 1986, "The Automatic Implantable Cardioverter–Defibrillator: Efficacy, Complications, and Device Failures".
Mau–Song Chang et al., JACC, vol. 8, –No. 6, Dec., 1986, pp. 1393–1405, "Double and Triple Sequential Shocks Reduce Ventricular Defibrillation and Threshold in Dogs With and Without Myocardial Infarction".
Charms et al., "Intracardiac Defibrillation", The Huron Road Hospital Medical Quarterly, Autumn, 1980, vol. 1, No. 4, pp. 2–6.

Primary Examiner—William E. Kamm
Attorney, Agent, or Firm—Renner, Otto, Boisselle & Sklar

[57] ABSTRACT

A bi-polar coaxial cable or catheter is passed transvenously into or proximate the heart, and the electrodes or poles of the cable are so positioned to apply electrical energy to the heart for defibrillation. Electrical energy input to the cable to effect defibrillation is in the form of a Lown wave. The invention also relates to a defibrillation method. A tri-axial cable catheter may be used for detecting fibrillation condition, defibrillation, and pacemaker functions. As space provides in the vein, additional leads may be included in the transvenous catheter for further monitoring and/or signal injecting purposes; and such leads may be of coaxial design. Further, as space provides, the catheter may include a hollow portion through which medicament may be conducted from outside the body directly into the heart and/or direct reading of central venous pressure may be effected.

20 Claims, 3 Drawing Sheets

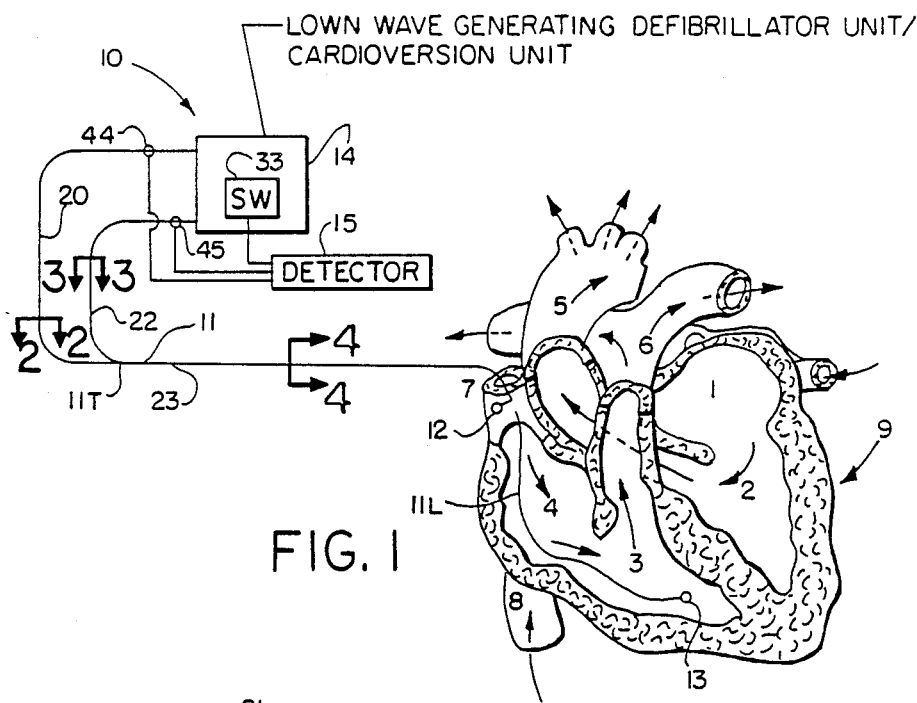
FIG. 1
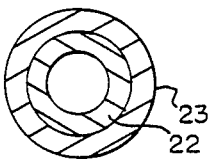
FIG. 2
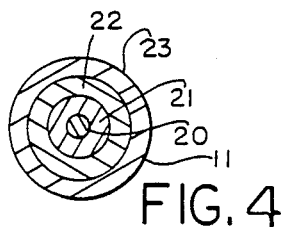
FIG. 3
FIG. 4
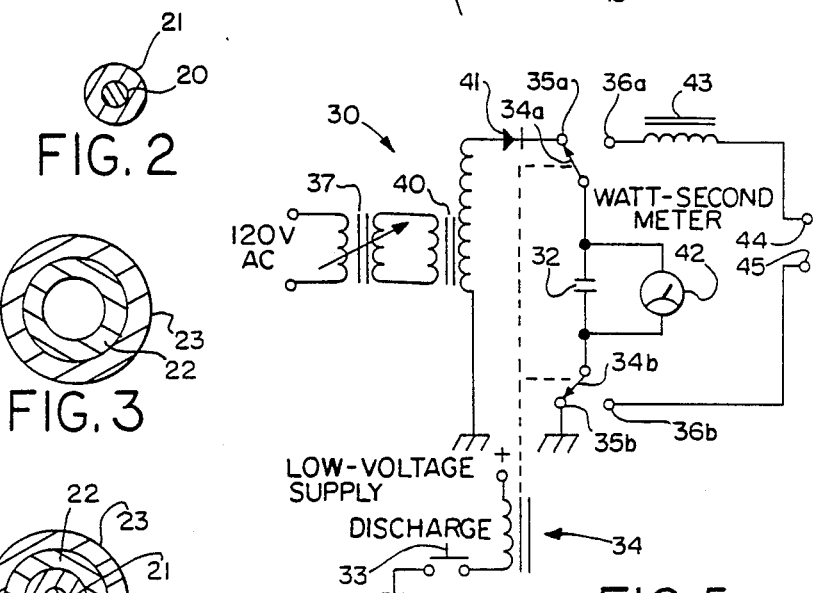
FIG. 5

APPARATUS AND METHOD OF DEFIBRILLATION

TECHNICAL FIELD

The present invention relates generally, as indicated, to apparatus and method for defibrillation of a heart and, more particularly, to the effecting of such defibrillation using a bi-polar coaxial cable or catheter positioned transvenously to place electrodes into or proximate the heart with electrical energization provided in the form of a wave shape of the type known as a Lown wave.

BACKGROUND

Reference is made to applicant's U.S. Pat. No. 3,738,370 which discloses the use of a coaxial cable catheter for placing electrodes in or near the heart using a transvenous technique. A sensor is provided to detect a fibrillation condition, and in response to such detection electrical energy is supplied through the coaxial cable to the electrodes to effect defibrillation. The entire disclosure of such patent hereby is incorporated by reference.

The terms defibrillation and cardioversion are used interchangeably and equivalently herein. It is, of course, known that both defibrillation and cardioversion apply electrical signals for overcoming a fibrillation or arrythmia condition. A primary difference between defibrillation and cardioversion is that in the latter a synchronization function is imposed to synchronize the applied shock with a particular signal detected from the heart.

The use of electrical energy to effect defibrillation of a heart has been known for some time. In addition to the bi-polar coaxial cable catheter approach previously disclosed by applicant in such patent, the application of electrical energy to the exterior of a patient's body, e.g. using a pair of conductive paddles, is one prior technique. Another technique is that in which one electrode is implanted using a transvenous path to the heart and a second electrode is surgically implanted in the chest cavity outside the heart. In all case it is desirable to provide adequate electrical energy or an electrical input of a particular characteristic that is adequately large, such as current or voltage, to effect defibrillation without damaging the heart or a part thereof.

One disadvantage to the "paddle" technique is that the equipment is not particularly portable, certainly not implantable, and another disadvantage is the relatively large amount of electrical energy required to effect defibrillation due to the impedance, for example 100 ohms, of the patient's body. The prior combination transvenous electrode and surgically implanted electrode technique requires less energy than the "paddle" technique for defibrillation, e.g. due to the reduced, about 50 ohms, impedance of the "exposed" heart; but the fact that surgical implantation is required itself is disadvantageous.

Various types of electrical signals (as used herein "electrical signals" means the actual electrical power or energy delivered for effecting defibrillation unless otherwise apparent from context) have been used for defibrillation. Examples include square wave forms, trapezoidal wave forms, wave forms derived from capacitor discharge through resistive impedance, wave forms derived from delay line coupling systems, and so on. Reference is made to the publication "Servicing Medical And Bioelectronic Equipment" by J. Carr, published by the George Washington University, February, 1977, pages 148–165, where a description of a Lown wave signal and circuitry for obtaining the same are presented. The entire disclosure of such publication hereby is incorporated by reference.

Also, various types of sensors may be used to detect a fibrillation condition to trigger operation of defibrillation equipment. Exemplary sensors and operating detector circuits for defibrillation equipment are disclosed in U.S. Pat. Nos. 4,184,493, 4,270,549, 4,393,877, and 4,559,546, the disclosures of which hereby are incorporated by reference.

BRIEF SUMMARY OF THE INVENTION

According to the present invention applicant has discovered that the Lown wave form of electrical signal is optimum electrical energy for defibrillation when using the transvenous bi-polar coaxial catheter defibrillation apparatus. Moreover, applicant has discovered that the trapezoidal and square wave forms generated by conventional implantable defibrillation apparatus tend not to work for acceptable defibrillation, i.e. to effect defibrillation without damaging the heart or with minimum damage, when using the bi-polar coaxial cable transvenously positioned catheter of the present invention.

According to one aspect of the present invention, then, a defibrillation apparatus, includes a bi-polar catheter having a pair of electrical conductors for conducting electrical energy, electrodes at or proximate one end of the catheter for delivering electrical energy for defibrillation, the catheter being positionable transvenously to position the electrodes at or within the heart, and a power supply for supplying electrical energy to said catheter in the form of an electrical signal consisting of a Lown wave. Moreover, according to the preferred embodiment and best mode of the present invention, the catheter is a coaxial cable that transmits the Lown wave along the same to the electrodes with minimum or accurately controlled signal dissipation while relatively accurately maintaining the shape of the Lown wave.

According to another aspect, a detector is provided for detecting a fibrillation condition of the heart, and a device responds to such detection for automatically effecting delivery of such Lown wave signal to effect defibrillation.

According to an additional aspect of the invention, a defibrillation method includes positioning a bi-polar catheter transvenously to place electrodes in or proximate the heart, and delivering electrical energy consisting of a Lown wave signal along said catheter to effect defibrillation. Consistent with the foregoing, preferably the catheter is a coaxial cable for the above reasons.

According to a further aspect, a defibrillation method includes detecting fibrillation of a heart, and delivering electrical energy consisting of a Lown wave along a bi-polar catheter positioned transvenously to place electrodes in or proximate the heart to effect defibrillation. Preferably such delivering uses the conductors of a coaxial cable.

According to still another aspect, a tri-lead or tri-axial cable catheter, i.e. one having three conductors, is positioned transvenously to locate the electrodes thereof at or in the heart, as above. However, two of the conductors and electrodes thereof are used for delivery of the defibrillation or cardioverting discharge signal or energy, and one of such conductors and associated electrode together with the third conductor and associated electrode are used for a pacemaker function. A pair of such conductors and electrodes also may be used for detection of a fibrillation or other fault condition of the heart. The Lown wave would be used for the defibrillation or cardioverting function; the detection and pacemaker functions may be carried out using conventional detection and/or pacemaker devices.

A still further aspect of the invention employs the coaxial cable catheter or triaxial cable catheter to deliver a defibrillation signal in the form of a Lown wave and to deliver a pacemaker impulse in the event of a complete cessation of cardiac activity, e.g. cardiac standstill, cardiac arrest or complete heart block.

A still additional aspect employs more than three leads in a transvenously inserted catheter to the heart for plural electrical input and/or monitoring functions.

Yet another aspect of the invention employs a hollow tube portion as part of the catheter, which also includes the several leads. The hollow tube may be employed to deliver medicament from outside the body directly into the heart and/or to monitor central venous pressure.

The foregoing and other aspects, features, objects and advantages of the present invention will become more apparent as the following description proceeds.

To the accomplishment of the foregoing and related ends, the invention, then, comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

In the annexed drawings:

FIG. 1 is a view, somewhat diagrammatic in nature, showing a coaxial cable catheter defibrillation apparatus of the present invention with a cut-away view of a heart showing the blood circulation and the manner in which the coaxial cable of the defibrillation apparatus of the present invention is introduced transvenously to place the electrodes in or proximate the heart;

FIG. 2 is a cross-sectional view, on an enlarged scale, taken on the line 2—2 of FIG. 1;

FIG. 3 is a cross-sectional view, on an enlarged scale, taken on the line 3—3 of FIG. 1;

FIG. 4 is a cross-sectional view, on an enlarged scale, taken on the line 4—4 of FIG. 1;

FIG. 5 is a schematic circuit diagram of an exemplary electrical circuit for generating a Lown wave;

DESCRIPTION OF THE PREFERRED EMBODIMENT

Figure 6:
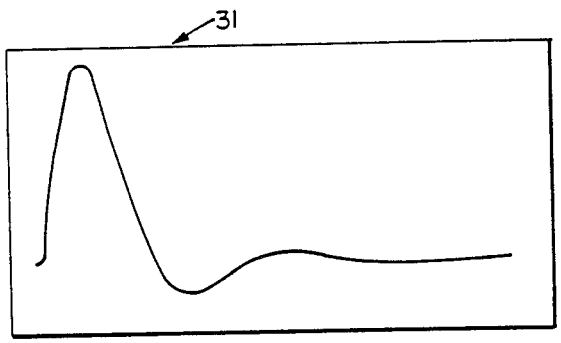
FIG. 6 is a graphical representation of a Lown wave signal used in the present invention.

Referring, now, in detail to the drawings, wherein like and primed reference numerals refer to like or similar parts in the several figures, and initially to FIG. 1, a heart is shown with the left atrium or auricle 1, left ventricle 2, right ventricle 3, right atrium or auricle 4, aorta 5, pulmonary artery 6, superior vena cava 7 and inferior vena cava 8. The heart itself is designated 9.

The defibrillating system of the present invention is generally designated 10. The system 10 includes a coaxial cable 11 sometimes referred to as a catheter because it is inserted transvenously, a pair of electrodes 12, 13 at one end of the cable, a Lown wave signal generating defibrillator unit 14, and a fibrillation detector 15.

The coaxial cable has a center lead wire or conductor 20, insulation 21 surrounding the wire 20, a tubular lead wire or conductor 22 surrounding the insulation 21, and a covering insulation 23 surrounding the wire 22. The wires 20, 22 may be of any metal which has excellent electrical transmitting properties. Such wire material should be completely compatible with body fluids so that when inserted the wire material does not cause irritation or have any other negative impact. The insulation 21, 23 may be any electrically insulative material that has good insulating properties and preferably also is completely compatible with body fluids to avoid irritation or other negative impact. Exemplary insulating material may be that sold under the trademark Teflon, which has desirable insulating and compatibility characteristics.

One particular advantage of a coaxial cable is the ability to select a specific characteristic impedance that can be maintained fairly accurately along the length of the cable. Another advantage is the ability of a coaxial cable to transmit electrical signals therealong with specifically calculatable and, thus, known, as well as relatively minimum, power loss. A further advantage is the ability to maintain fairly accurately the characteristics of an electrical signal as it is transmitted along the coaxial cable. These characteristics are advantageous not only when the coaxial cable is used by transvenous insertion for heart defibrillation, but, more specifically, when it is desired to maintain the shape, power, and duration of the specific Lown wave signal according to the present invention.

In using the defibrillation system 10 of the invention, the coaxial cable 11 is inserted into a vein, e.g. branch of the right or left external jugular or subclavian, and is passed transvenously through the superior vena cava. According to the preferred embodiment and best mode of the invention, the electrodes 12, 13 are positioned in the heart or great vessels, for example in the right atrium (or auricle) and/or the right ventricle to apply electrical energy there to effect defibrillation. However, it will be appreciated that the electrodes 12, 13 may be placed in other chambers of the heart or outside the heart or each electrode may be placed in a different respective chamber or one in a chamber and the other outside the heart, e.g. still in the vein; and appropriate electrical energy may be provided to effect the desired function. As a further example, one of the electrodes 12, 13 may be placed at the apex of the ventricle 3 distally and the other of the electrodes 12, 13 in the superior vena cava 7 proximally, i.e. relative to the detection and defibrillation unit 14, 15, as is illustrated in FIG. 1.

According to the preferred embodiment and best mode of the invention, though, using such transvenous insertion of the coaxial cable catheter the distal electrode 13 is placed directly in the right ventricle 3 and the proximal electrode 12 is placed in the superior vena cava 7; it has been found that application of a Lown wave signal to such electrodes so placed will have the most repeatable results for ventricular defibrillation purposes.

Prior to insertion of the coaxial cable catheter 11 transvenously, the electrodes 12, 13 are formed or are placed at the leading end 11L of the cable. For this purpose, a portion of the insulation 21, 23 is removed to expose the respective wires 20, 22, and such exposed wire conductors then may constitute the respective electrodes 12. However, if desired, separate electrodes of electrically conductive material may be attached to the ends of the wires 20, 22.

Preferably the leading portion 11L of the cable 11 is within the right ventricle of the heart, so as to lie closely adjacent the inner wall of such chamber. The electrodes 12, 13 are spaced apart and electrically insulated from each other, as is illustrated, with the proximal electrode 12 in the superior vena cava 7 and the distal electrode 13 in the right ventricle 3. It is desirable that the electrodes 12, 13 be at a maximum distance from each other along the long axis of the heart. The Lown wave electrical signal appears to exert a maximum defibrillatory action, for example being active along substantially the entire length of the heart muscle. It has been found that the electrodes 12, 13 may be positioned in closer proximity to each other than just described. However, as the electrodes are brought closer to each the magnitude of at least one parameter of the electrical signal would have to be increased to provide the desired defibrillation result; and to avoid damage to the heart (or other part of the body) by the electrical signal it is desirable to minimize the magnitude and/or energy of the signal while maintaining an adequate level to carry out defibrillation. Of course, the distance between the electrodes 12, 13 will be a function of the size of the chamber and/or of whether both electrodes are in a single chamber.

As one example, the electrodes 12, 13 may be spaced in the manner shown in FIG. 1 at a distance from each other of from about 8 to about 10 cm. In such example, the terminal voltage supplied by the unit 14 may be as high as about 500 volts, i.e. the maximum peak of the Lown wave signal. The total time duration of such Lown wave signal may be from about 10 to about 25 milliseconds applying from about 10 to about 40 joules of energy to achieve ventricular defibrillation.

The trailing end 11T of the coaxial cable catheter 11 is connected to the Lown wave generating defibrillator unit 14, an exemplary circuit schematic of which is described below with reference to FIG. 5. More specifically, each of the conductors 20, 22 is connected to the output of the unit 14 to receive a Lown wave signal that is conducted along the cable 11 and is delivered directly to the heart 9 by the electrodes 12, 13. Due to the above-mentioned desirable characteristics of the coaxial cable 11, such Lown wave signal maintains its power and/or other characteristics level and its shape at the point of delivery in the heart 9 to accomplish effective and efficient defibrillation. Moreover, such coaxial cable conductors may be used to provide information to the detector unit 15 to detect the occurrence of a fibrillation, arrythmia, or possibly other fault concrion. In such case, for protection of the detector unit 15 it would include a conventional switch over circuit that would temporarily disengage or disconnect the detector unit when the defibrillator unit or cardioversion unit 14 is providing the higher level signal to the cable during defibrillation. At the conclusion of defibrillation, such switch over circuit would re-couple the detector unit 15 in operative relation to the lead conductors 20, 22 to continue detecting function. Exemplary detectors that may be used as the fibrillation detector 15 are disclosed in the above-mentioned patents, which are incorporated by reference. Detectors useful according to the invention also include those manufactured and/or sold by Intec Corporation, which currently is owned by Eli Lilly Company.

Thus, in operation of the system 10, equipment, such as detector 15, may detect an arrythmia, for example fibrillation condition; and such detector causes the unit 14 to deliver appropriate electrical energy, e.g. in the form of a Lown wave signal, along leads 20, 22 directly to the electrodes 12, 13 in the heart 9 to effect defibrillation or otherwise to stop the arrythmia and to allow or to cause normal heart function to resume. Alternatively, external equipment of conventional design may be used to detect the arrythmia and to effect automatic operation of the unit 14 to deliver appropriate electric energy or signal to the heart 9.

If desired, the catheter 11 may be of a type other than coaxial cable, e.g. a pair of parallel conductors or a twisted pair of conductors, passed transvenously in the same way as the coaxial cable 11 described in detail above. In such case, though, the characteristics, e.g. shape and magnitude, of the Lown wave signal at the point of delivery to the heart may not be as accurately controlled or represented relative to the characteristics of such Lown wave signal at the point of connection from the unit 14 to the conductors and, thus, may result in less satisfactory repeatable defibrillation effect than the preferred coaxial cable described herein.

The invention also envisions the use of a pair of conductors (not in coaxial or twisted pair configuration) inserted transvenously to the heart, as above, and a Lown wave generating circuit to provide a Lown wave signal to effect defibrillation. However, such embodiment would not have the advantages of using a coaxial or triaxial cable or even twisted pair conductors; and it is to be understood that this is a less preferred embodiment of the invention.

Briefly referring to FIG. 5, a relatively simple circuit 30 is shown as an example of one that may be used in or as the Lown wave generating defibrillator unit/cardioversion unit 14 to generate the Lown wave 31 of FIG. 6 to effect defibrillation according to the invention. Other forms of circuits, some of which may be more sophisticated than the circuit 30 also may be employed according to the invention to generate a Lown wave or Lown type wave to effect the operative defibrillation using the transvenous catheter arrangement of the present invention.

In the circuit 30 a capacitor 32 is used to store energy; such capacitor may be, for example, a 16 microfarad capacitor of the high voltage and oil-filled type. To charge the capacitor 32, a push button switch 33 is open and a high voltage relay 34 is deenergized. Accordingly, the two switch arms 34a, 34b of the relay 34 are coupled to the contacts 35a, 35b, as is shown in the drawing; and contacts 36a, 36b are effectively disconnected from receiving power. In this configuration of the circuit 30, power applied to a variable transformer 37 from a power source 38 is in turn coupled via a transformer 40 to charge the capacitor 32 via the diode 41. A meter 42, such as a kilovoltmeter, indicates the charge on the capacitor 32 and is calibrated in watt-seconds to indicate useful information to the user indicating whether or not the capacitor is charged to a level suitable to effect defibrillation. In the portable unit of the present invention, though, it ordinarily would be unnecessary to include a meter with the circuit 30. According to the invention, though, it would be desirable to maintain the capacitor 32 charged to a level ready to effect delivery of a suitable Lown wave capable of causing defibrillation.

When delivery of the Lown wave output from the circuit 30 is desired, e.g. when an operator closes the switch 33 or a detector 15 causes an effectively automatic closing of the switch 33 or equivalent activity to produce a Lown wave, the switch arms 34a, 34b open circuit connection with the contacts 35a, 35b and close circuit connection with the contacts 36a, 36b. The capacitor 32 then discharges through a series circuit that includes an inductor 43 and output terminals 44, 45, which are connected to the leads 12, 13 of the coaxial cable catheter 11.

Using, for example, a 16 microfarad capacitor 32 and a 100 millihenry inductor 43 and a circuit resistance that essentially is the sum of the resistance of the inductor 43, relay 34 contact resistance, characteristic impedance of the coaxial cable 11, and 31, as is shown in FIG. 6. Such Lown wave signal may have an energy or power of about 400 watt-seconds. The actual main positive portion of the Lown wave 31 may have a rise time less than about 500 microsecond and a peak amplitude on the order of about 3000 volts. Such main positive pulse ordinarily is competed in about 5 milliseconds. The magnetic field of the inductor 43 will discharge or collapse following the main pulse so as to cause a negative undershoot that may last approximately an additional 5 milliseconds. As is evident from FIG. 6, then, the Lown wave signal is a highly damped wave form.

It will be appreciated that the circuit 30 and Lown wave 31 are exemplary. Other circuits may be employed for the purpose of generating a signal having the highly damped Lown wave characteristic at appropriate amplitudes and time characteristics to effect defibrillation in accordance with the invention.

The Lown wave generating defibrillator unit 14 preferably is capable of providing electrical energy at a level of from about 10 to about 400 watt seconds (joules). The unit also is intended to provide such electrical energy over a controlled time period of from about 3 to about 100 milliseconds, or even longer. Preferably the duration of the Lown wave signal is from about 3 to about 50 milliseconds in duration; however, such duration may be longer depending on the characteristic impedance of the cable 11 and/or the impedance characteristics of the space or environment between the electrodes 12, 13. Desirably, though, the duration of application of the Lown wave signal should be adequate to effect defibrillation without damaging the heart 9 or other part of the body of the patient.

Preferably the Lown wave generating defibrillator unit 14 is portable; indeed, most preferably such unit is capable of being implanted in the patient or of being worn at all times. Consistent with such portability, such unit 14 preferably is powered by a battery.

By reducing the requirements for insulation due to use of a coaxial cable, it becomes possible to utilize a permanently implantable self-contained power unit, which could be set to determine the presence of an absent, too-rapid or irregular heart beat, and deliver an appropriate shock synchronized. The energy required for such a unit can be derived from an inductively rechargable battery source connected to a series of condenser plates for storage of the charge.

Although the invention has been described with particular reference to the use of a bi-polar coaxial cable, it is to be understood that any cable containing two wires in parallel spaced arrangement with each other, but fully insulated from each other, may be used, or, for that matter, insulated wires which are entirely separated from each other may be used. The important desideratum is the placement of the wire or wires (i.e. electrodes), according to the preferred embodiment and best mode of the invention, either in the atrium, or in the ventricle and superior vena cava. However, most preferred for the reasons stated herein, e.g. minimum signal distortion and minimum power loss, is the coaxial cable configuration for a bi-polar or two lead cable, or, if more than two leads are used, a tri-axial, or further multi-axial cable configuration.

Moreover, although the invention of the system 10 of FIG. 1 has been described with reference to use to effect defibrillation and also to detect a fibrillation condition, it will be appreciated that the units 14 and 15 may be of the type that deliver electrical signals for pacemaker function and defibrillation function, as required, and to detect the need for a pacemaker function (and timing therefor) and defibrillation function, respectively. In such case, the circuit 14 would include conventional pacemaker circuitry, for example, as well as the Lown wave generating circuitry described herein. The circuit 15 would the modified to detect the need for and/or timing of pacemaker function and the need for defibrillation function. Also, the electrodes 12, 13 would be positioned to try to optimize to the extent possible the proper application of both defibrillation and pacemaker signals.

Figure 7:
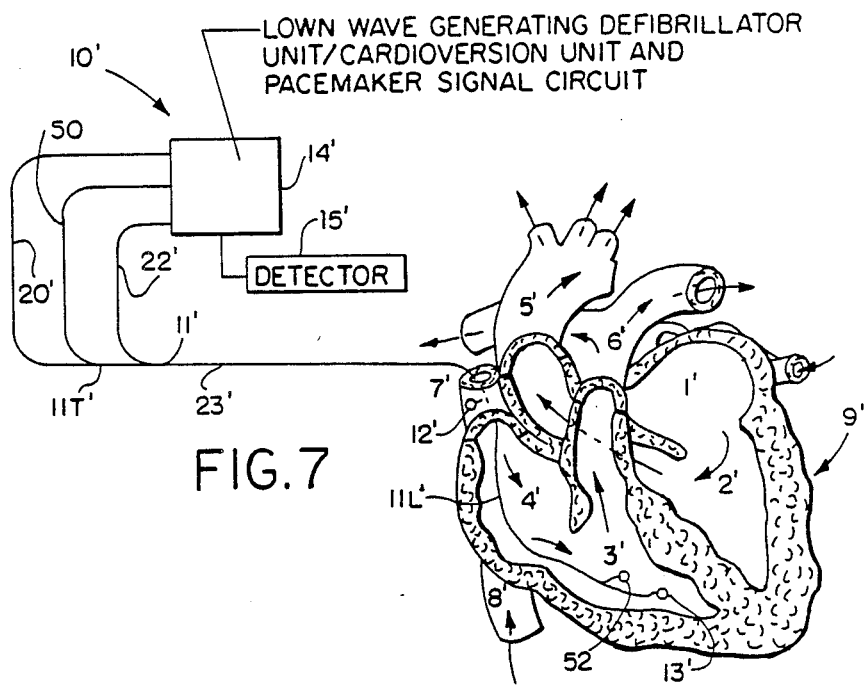
FIG. 7 is a schematic illustration similar to FIG. 1 but showing a triaxial cable catheter used in accordance with an alternate embodiment of the invention.

Turning briefly to FIG. 7, a modified defibrillating system 10' is illustrated. The various parts of the system 10' similar in structure and/or function to corresponding parts of the system 10 described above with reference to FIG. 1, for example, are identified by the same reference numerals, although the same have been indicated with a prime (') notation. In the system 10' the cable catheter 11' is a triaxial cable catheter, which includes leads 20', 22' and a third lead 50. Such leads are assembled in conventional triaxial configuration, as is well known, i.e. one lead is in the center, a second is concentric therewith and spaced therefrom by electrical insulation, and a third is concentric with the first and second and is spaced from the second by electrical insulation. Each such lead terminates at one end in the unit 14' and at the other end in a respective electrode 12', 13', 52.

Operation of the system 10' is generally similar to operation of the system 10. However, two of the three leads 20', 22' and 50 may be used with the corresponding two of the electrodes 12', 13' and 52 to deliver the Lown wave for defibrillation. Two of the leads and corresponding electrodes may be used to couple information to the detector 15' to detect heart function or malfunction. Also, two of the leads and corresponding electrodes may be used to effect conventional pacemaker function; in this regard the detector 15' would be appropriate one to detect the need and/or timing required for pacemaker function and the unit 14' would be of the type that could also deliver appropriate signals to respective electrodes for pacemaker functions. It is noted here that the minimal signal distortion and maximized power transmission capabilities of the multi-axial (e.g. tri-axial) cable further enhances accurate operation of the multiple functions of the disclosed system. Positioning and spacing of the two electrodes 12', 13' for defibrillation function would be as was described above. Spacing and positioning of two electrodes, e.g. electrode 52 and electrode 13', would be generally in the manner typically used for pacemaker electrodes, for example as is illustrated in FIG. 7 with the electrode 52 much more proximate the electrode 13' than the relatively large spacing of the defibrillating electrodes 12', 13'.

Figure 8:
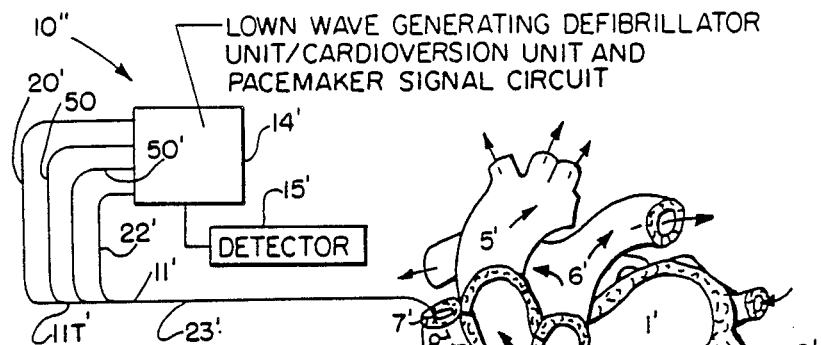
FIG. 8 is a schematic illustration similar to FIG. 1 but showing a device with more than three leads.

Turning briefly to FIG. 8, a further embodiment of the present invention is illustrated. The system 10" is similar to the system 10' except the system 10" has an additional conductor or lead 50, terminating at one end in the unit 14' and at the other end in an electrode 52'. Thus, in the system 10" one electrode 12' is positioned in the superior vena cava 7'; one electrode is positioned in the right ventricle 3'; and the electrodes 52, 52' are in the right atrium 4'. Actual positions of the electrodes may be determined according to function thereof, known techniques, and/or pragmatic results. For example, the wide spacing of electrodes 12', 13' provides excellent defibrillation function with a Lown wave delivered thereacross, as was described above. Two of the electrodes may be used to sense heart function; two may be used for pacemaker function; etc. Importantly, though, the multiple conductor leads 20', 22', 50, 50' (and those of the other embodiments herein) are inserted transvenously, thus avoiding the need to open the chest cavity for implantation, and preferably the leads are of the multi-axial type to achieve the desired electrical characteristics mentioned above, to minimize space requirements in the vein, and to facilitate insertion. The detector 15' may include conventional circuitry to sense heart function, e.g. proper function, an arrythmia, etc., and/or to operate alone or with the unit 14' to effect a timing function for pacemaker operation.

Figure 9:
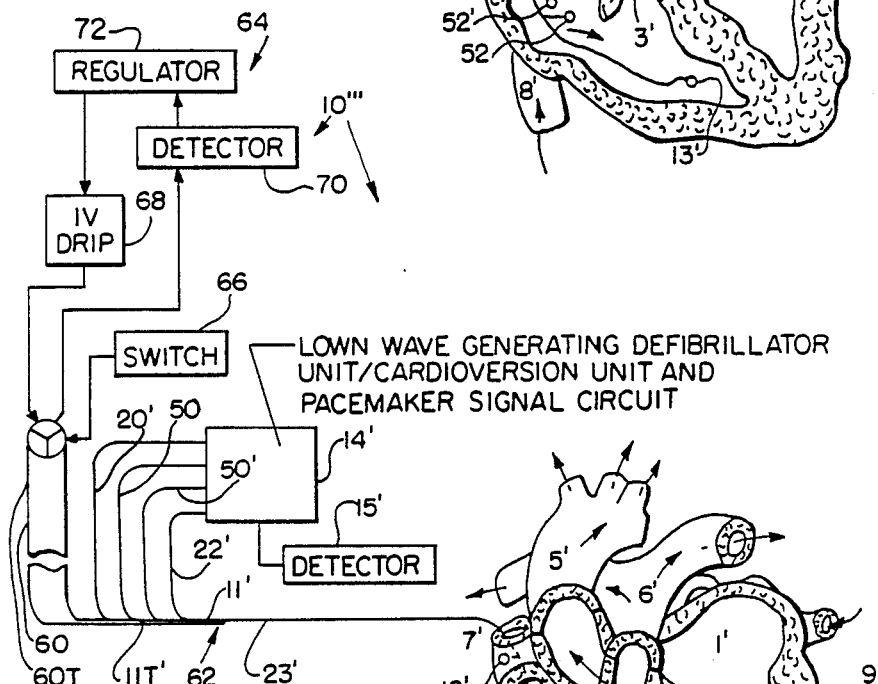
FIG. 9 is a schematic illustration of an alternate embodiment employing as part of the catheter a hollow tube for inserting medicament and/or for monitoring central venous pressure.

In FIG. 9 is a still further embodiment of the invention. A system 10''', includes a multi-axial cable 3 catheter, e.g. of coaxial, tri-axial, or quad-axial type, as in FIGS. 1, 7, or 8, with unit 14, and detector 15, and the several electrodes all operative generally as was described above. Additionally, the system 10''' includes a fluid conducting catheter or tube 60, which is coupled or bundled with the conductor leads 20', 22', 50, 50', etc., to form a transvenously insertable composite catheter 62. The leading end 60L of the fluid conducting catheter 60 is located in the heart (or, if desired, in the vein into which the catheter 62 is inserted), and the trailing end 60T is exposed, for example, outside the heart, preferably outside the body of a patient, for purposes described below.

The system 10''' includes a fluid system 64 associated with the fluid conducting catheter 60. Such system 64 may include a flow control switch 66 to open and/or to close access to the catheter 60 and/or to determine what other parts of the fluid system 64 is/are fluidically coupled thereto; an intravenous drip system 68 for providing an IV (intravenous) drip to the catheter 60 for direct delivery into the heart 9; a detector 70 for detecting central venous pressure, for example, directly in the right atrium 4 of the heart; and a regulator 72 for controlling the IV drip rate, for example, as a function of detected central venous pressure. The fluid conducting catheter 60 may include one flow path or several parallel fluidically separate flow paths to permit simultaneous monitoring of central venous pressure and delivering of an IV drip.

The detector 70 may be a conventional detector for detecting fluid pressure. The regulator 72 and IV drip 68 may be conventional IV apparatus. In the case of operation of the regulator in response to the detector 70 output, the detector and regulator may be electrically coupled so that the detector output causes a prescribed regulation level by the regulator to control the IV drip 68 and rate of fluid input the heart, e.g. as a function of monitored pressure.

The leading end 60L of the fluid conducting catheter 60 may be located at various positions in the heart 9 or outside thereof, for example, to provide the IV drip directly to such locations. Moreover, the catheter 60 may be along side of the multi-axial cable 11' or therewithin, e.g. forming a hollow tube or annular cross-sectional part thereof. In any event it is preferred that the fluid and electrical portions of the catheter 62 be inserted simultaneously transvenously to the heart generally as has been described herein; and for that purpose such parts preferably are formed as a unified catheter device or are coupled together in the mentioned common axial or side by side configuration.

Use of the system 10''' electrically would be generally as was described above. Use fluidically may be carried out to monitor pressure, to deliver an IV drip, and to effect control of the latter. Due to the larger cross-sectional size of the composite catheter 62 over those without the fluid conducting catheter 60 and due to the possible exposure of the flow path therein at the trailing end 60T, it is preferred that the system 10''' be used primarily in a relatively controlled environment, such as in a hospital coronary care unit or other relatively limited access facility; and it also is anticipated that generally the catheter 62 would be removed prior to full patient release from medical care. It will be appreciate, though, that under relatively careful conditions, the system 10''' may be used outside such limited or controlled environment. Moreover, it will also be appreciated that the other systems 10, 10' and 10" described above are rather portable and may be used by a patient even outside a controlled environment especially for automatic use in the event of an arrythmia occurring quite unexpectedly.

It is to be understood that various changes in the method and apparatus which has been described may be made without departing from the spirit of the invention and the scope of the appended claims.

STATEMENT OF INDUSTRIAL APPLICATION

In view of the foregoing, it will be appreciated that the apparatus and method described in detail may be employed to effect defibrillation of a heart.

I claim:

1. Defibrillation apparatus, comprising a bipolar catheter means having a pair of electrical conductors for conducting electrical energy, electrode means at one end of said catheter means for delivering electrical energy for defibrillation, said catheter means being positionable transvenously to position said electrode means at the heart to enable said electrode means to apply electrical shock to the heart to effect defibrillation, and Lown wave generating power supply means for supplying electrical energy to said catheter means in the form of an electrical signal consisting of a Lown waveform, wherein said catheter means is positionable transvenously to position said electrode means entirely in intravascular and intracardiac relation to a heart of a patient, and wherein said electrode means include a pair of electrodes that are spaced apart a distance for placement of one in the right ventricle and the other in the superior vena cava.

2. The apparatus of claim 1, said bipolar catheter means comprising a coaxial cable.

3. The apparatus of claim 1, further comprising detector means connected to conductors of said catheter means for detecting a fibrillation condition of the heart, and said detector means being responsive to such detection and being coupled to said power supply means for automatically effecting delivery of such Lown wave signal to effect defibrillation.

4. The apparatus of claim 1, further comprising detector means connected to said conductors of said bipolar catheter means to detect arrythmia and to cause operation of said power supply means to supply electrical energy to said catheter means to effect defibrillation.

5. The apparatus of claim 1, said bipolar catheter means, power supply means, and electrode means includes means further to provide pacemaker impulse in the event of complete cessation of cardiac electrical activity.

6. Defibrillation method for a patient, comprising positioning a bi-polar catheter which has plural conductors and electrodes coupled to plural conductors thereof transvenously to place plural electrodes in or proximate the heart, wherein said positioning comprises positioning one of such electrodes into the ventricle and the other in the superior vena cava, and delivering electrical energy consisting of a Lown wave signal along said catheter to effect defibrillation by a shock delivered to the heart by such electrodes therein.

7. The method of claim 6, said positioning comprising, positioning a coaxial cable transvenously, and said delivering comprising delivering such Lown wave signal along the conductors of such coaxial cable to such electrodes.

8. The method of claim 7, further comprising detecting a fibrillation condition, and wherein said delivering comprises automatically in response to such detection effecting delivery of such Lown wave signal to effect defibrillation.

9. The method of claim 6, wherein said delivering comprises delivering such electrical energy at a level of from about 10 watt seconds to about 40 watt-seconds.

10. Defibrillation apparatus, comprising a bi-polar catheter means having a pair of electrical conductors for conducting electrical energy, electrode means at one end of said catheter means for delivering electrical energy for defibrillation, said catheter means being positionable transvenously to position said electrode means at the heart of a person in intravascular and intracardiac relation to enable said electrode means to apply electrical shock to the heart to effect defibrillation, wherein said electrode means include a pair of electrodes that are spaced apart a distance for placement of one in the right ventricle and the other in the superior vena cava, and electrical power supply means for supplying electrical energy to said catheter means in the form of an electrical signal consisting of a waveform that has an initial relatively large magnitude positive polarity curved peak portion followed by a much smaller magnitude negative polarity curved peak portion.

11. Defibrillation apparatus for a patient, comprising a bi-polar catheter means having a pair of electrical conductors for conducting electrical energy, a pair of electrodes at one end of said catheter means for delivering electrical energy for defibrillation, said catheter means being positionable transvenously to position said electrodes respectively in the right ventricle of the heart and in the superior vena cava to enable said electrodes to apply electrical shock directly to the heart to effect defibrillation, said electrodes being spaced apart for said positioning, respectively, in the right ventricle and superior vena cava, and power supply means for supplying electrical energy to said catheter means to effect such defibrillation.

12. The apparatus of claim 11, wherein said power supply means consists of a Lown wave generating circuit means for providing an electrical signal in the form of an electrical signal consisting of a Lown waveform.

13. Defibrillation method, comprising positioning a bi-polar catheter which has plural conductors and electrodes coupled to respective plural conductors thereof transvenously to place plural electrodes entirely in intercardiac and intravascular relation to the heart, wherein said positioning comprises positioning one of such electrodes in the ventricle and the other in the superior vena cava, and delivering electrical energy along said catheter to effect defibrillation by a shock delivered to the heart by such electrodes, said delivering comprising delivering a Lown wave type signal to plural conductors of said catheter.

14. Defibrillation method, comprising positioning a bi-polar catheter which has plural conductors and electrodes coupled to respective plural conductors thereof transvenously to place plural electrodes entirely in intercardiac and intravascular relation to the heart, wherein said positioning comprises positioning one of such electrodes in the ventricle and the other in the superior vena cava, and delivering electrical energy along said catheter to effect defibrillation by a shock delivered to the heart by such electrodes, said delivering comprising delivering such electrical energy at a level of from about 10 watt-seconds to about 40 watt-seconds.

15. The method of claim 14, wherein said delivering comprises delivering such electrical energy for a time duration of from about 10 milliseconds to about 25 milliseconds.

16. The method of claim 9, wherein said delivering comprises delivering such electrical energy for a time duration of from about 10 milliseconds to about 25 milliseconds.

17. In a defibrillation method in which a bi-polar catheter having electrodes is positioned transvenously to place electrodes thereof relative to the heart, the improvement comprising placing a pair of such electrodes respectively in the ventricle and in the superior vena cava of a heart, detecting fibrillation of the heart, and delivery electrical energy along such bi-polar catheter while said electrodes remain so positioned to effect defibrillation, said delivering comprising delivering such electrical energy at a level of from about 10 watt-seconds to about 40 watt-seconds.

18. The method of claim 17, wherein said delivering comprises delivering such electrical energy for a time duration of from about 10 milliseconds to about 25 milliseconds.

19. Defibrillation method, comprising positioning a bi-polar catheter which has plural conductors and electrodes coupled to respective plural conductors thereof transvenously to place plural electrodes entirely in intercardiac and intravascular relation to the heart, wherein said positioning comprises positioning one of such electrodes in the ventricle and the other in the superior vena cava, and delivering electrical energy along said catheter to effect defibrillation by a shock delivered to the heart by such electrodes, said delivering comprising delivering an electrical signal consisting of a waveform that has an initial relatively large magnitude positive polarity curved peak portion followed by a much smaller magnitude negative polarity curved peak portion.

20. In a defibrillation method in which a bi-polar catheter having electrodes is positioned transvenously to place electrodes thereof relative to the heart, the improvement comprising placing a pair of such electrodes respectively in the ventricle and in the superior vena cava of a heart, detecting fibrillation of the heart, and delivery electrical energy along such bi-polar catheter while said electrodes remain so positioned to effect defibrillation, said delivering comprising delivering an electrical signal consisting of a waveform that has an initial relatively large magnitude positive polarity curved peak portion followed by a much smaller magnitude negative polarity curved peak portion.

* * * * *